(12) United States Patent
Nariyuki et al.

(10) Patent No.: US 9,883,839 B2
(45) Date of Patent: Feb. 6, 2018

(54) RADIOGRAPHIC IMAGING DEVICE

(71) Applicant: FUJIFILM Corporation, Tokyo (JP)

(72) Inventors: Fumito Nariyuki, Kanagawa (JP);
Haruyasu Nakatsugawa, Kanagawa (JP); Takafumi Hironaka, Kanagawa (JP); Satoshi Tanaka, Kanagawa (JP); Michihiro Shibata, Kanagawa (JP); Hideo Nagasaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 320 days.

(21) Appl. No.: 14/790,002

(22) Filed: Jul. 2, 2015

(65) Prior Publication Data

US 2015/0327823 A1 Nov. 19, 2015

Related U.S. Application Data

(63) Continuation of application No. PCT/JP2014/051995, filed on Jan. 29, 2014.

(30) Foreign Application Priority Data

Jan. 30, 2013 (JP) ................... 2013-016158
Jul. 5, 2013 (JP) ................... 2013-141896
Jan. 28, 2014 (JP) ................... 2014-013790

(51) Int. Cl.
*A61B 6/00* (2006.01)
*A61B 6/04* (2006.01)
*G03B 42/04* (2006.01)

(52) U.S. Cl.
CPC .......... *A61B 6/0414* (2013.01); *A61B 6/4283* (2013.01); *A61B 6/4423* (2013.01); *A61B 6/502* (2013.01); *G03B 42/04* (2013.01)

(58) Field of Classification Search
None
See application file for complete search history.

(56) References Cited

U.S. PATENT DOCUMENTS

| 6,436,422 B1 * | 8/2002 | Trogolo ............... A61L 29/106 |
| | | 424/404 |
| 6,577,702 B1 * | 6/2003 | Lebovic ............... A61B 6/0414 |
| | | 378/208 |
| 9,034,489 B2 | 5/2015 | Jing et al. |

(Continued)

FOREIGN PATENT DOCUMENTS

| JP | H07-313561 | 12/1995 |
| JP | 2003-207864 | 7/2003 |

(Continued)

OTHER PUBLICATIONS

"First Office Action of China Counterpart Application" with English translation thereof, dated Feb. 24, 2017, p. 1-p. 15.

(Continued)

*Primary Examiner* — Hoon Song
(74) *Attorney, Agent, or Firm* — JCIPRNET

(57) ABSTRACT

A radiation imaging apparatus includes a hydrophilized portion provided on at least a portion of an outer surface of the radiation imaging apparatus. The hydrophilized portion contains a hydrophilic polymer and an antibacterial agent. A water contact angle of a surface of the hydrophilized portion is equal to or less than 30°.

14 Claims, 5 Drawing Sheets

(56) References Cited

U.S. PATENT DOCUMENTS

| | | | |
|---|---|---|---|
| 2005/0051447 A1* | 3/2005 | Nakajo | G03C 3/00 206/455 |
| 2009/0220055 A1 | 9/2009 | Nakata et al. | |
| 2010/0092765 A1 | 4/2010 | Hager et al. | |
| 2013/0189516 A1 | 7/2013 | Sugino et al. | |

FOREIGN PATENT DOCUMENTS

| | | |
|---|---|---|
| JP | 2005-275293 | 10/2005 |
| JP | 2009-207561 | 9/2009 |
| JP | 2012-505295 | 3/2012 |
| JP | 2012-123297 | 6/2012 |
| JP | 2012-132703 | 7/2012 |
| JP | 2012-532214 | 12/2012 |
| WO | 2012/049886 | 4/2012 |

OTHER PUBLICATIONS

"Written Opinion of the International Searching Authority of PCT/JP2014/051995", this report contains the following items: Form PCT/ISA237(cover sheet), PCT/ISA237(Box No. I), PCT/ISA237(Box No. V), dated Mar. 25, 2014, which is English translation of "Written Opinion of the International Searching Authority", pp. 1-8.

"International Search Report (Form PCT/ISA/210)", dated Mar. 25, 2014, with English translation thereof, pp. 1-4.

"Office Action of Japan Counterpart Application," dated May 17, 2016, with English machine translation thereof, p. 1-p. 7.

"Office Action of China Counterpart Application," with English translation thereof, dated Oct. 9, 2017, p. 1-p. 16.

* cited by examiner

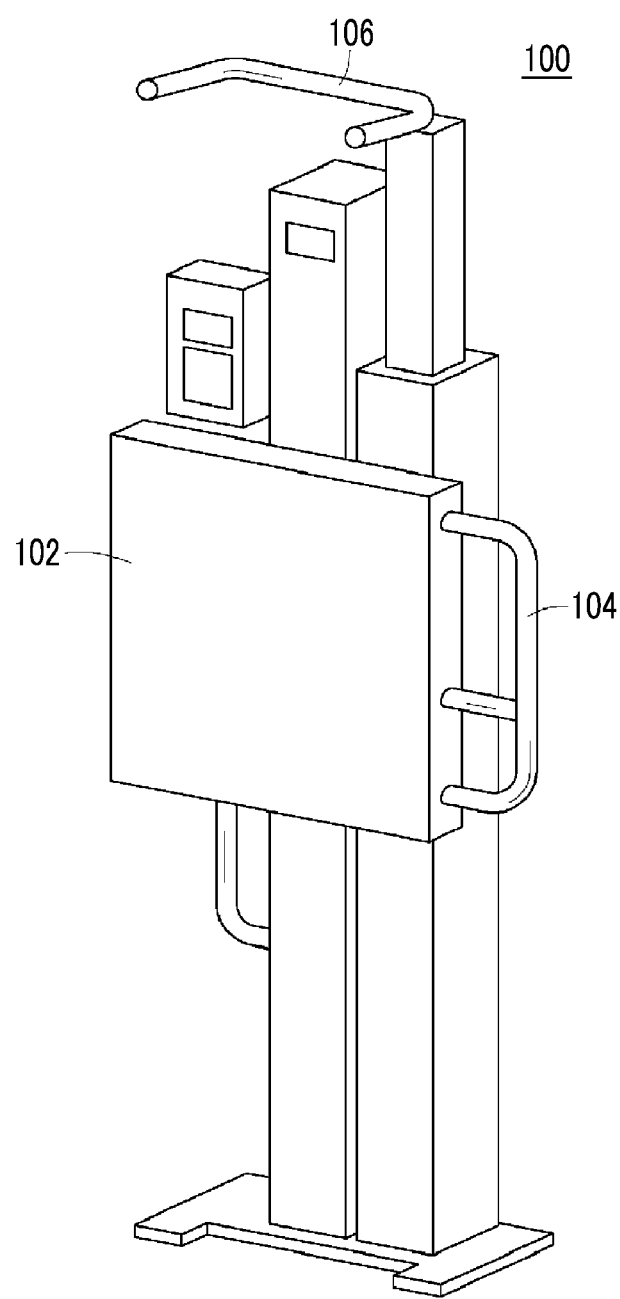

RADIOGRAPHIC IMAGING DEVICE

CROSS-REFERENCE TO RELATED APPLICATIONS

This application is a Continuation of PCT International Application No. PCT/JP2014/051995 filed on Jan. 29, 2014, which claims priority under 35 U.S.C §119(a) to Japanese Patent Application No. 2013-016158 filed on Jan. 30, 2013, Japanese Patent Application No. 2013-141896 filed on Jul. 5, 2013, and Japanese Patent Application No. 2014-013790 filed on Jan. 28, 2014. Each of the above applications is hereby expressly incorporated by reference, in its entirety, into the present application.

BACKGROUND OF THE INVENTION

1. Field of the Invention

The present invention relates to a radiation imaging apparatus including a hydrophilized portion provided in at least a portion of the outer surface thereof 2. Description of the Related Art Many of medical apparatuses used in the medical field are continuously brought into contact with a plurality of patients. Particularly, radiation imaging apparatuses are continuously used for a plurality of patients. When the body fluid or the like of the patients adheres to these medical apparatuses and are insufficiently cleaned or washed therefrom, a pathogenic viral infection and the like may be transmitted between the patients or between the patient and a radiographer. In order to prevent such infection, the surface of the medical apparatus is sterilized by using a disinfectant solution such as an aqueous ethanol solution or an aqueous sodium hypochlorite solution, regularly or whenever the apparatus is used for a new patient when there is a high risk of infection.

When the radiation imaging apparatus, especially, a portable radiation imaging apparatus is used in an operating room, an emergency room, or the like, blood or vomit containing infectious viruses or bacteria, body fluid, sebum, and the like adhere to the apparatus in some cases. Furthermore, in the case of a mammography apparatus, lipstick or sebum from a patient adheres to a face guard portion, or oozing breast milk, blood resulting from a hemorrhage at the time of biopsy (mammotome biopsy), or sebum adheres to a breast support or a breast compression plate. These types of contaminants from patients are not easily wiped off. Particularly, in some cases, the contaminants are stuck to the surface of the apparatus, so it takes time to wipe the contaminants off As solutions to these problems, the following techniques have been suggested.

For example, JP2012-132703A discloses a technique of mounting a waterproofed buffer material on the outer surface of a medical instrument. According to the technique, an advantage such that a contaminant does not easily adhere to the medical instrument is obtained.

JP2012-123297A suggests a method of covering a medical instrument with a photocatalyst (for example, $TiO_2$) that has a bactericidal action.

Moreover, as suggested in JP1995-313561A (JP-H07-313561A), JP2005-275293A, and JP2003-207864A, as a countermeasure for infection, a method of performing antibacterial processing on various medical instruments including a radiation imaging apparatus has been considered.

SUMMARY OF THE INVENTION

However, in view of sterilization, the technique described in JP2012-132703 reduces the wettability of the surface of the medical apparatus with respect to the disinfectant solution. That is, because the disinfectant solution bounces off, it is not easy for the disinfectant solution to stay on the outer surface of the medical apparatus for a long period of time, and accordingly, a sufficient sterilizing effect on bacteria is not highly likely to be obtained.

The photocatalyst described in JP2012-123297A is known to exhibit both the bactericidal effect and hydrophilicity. However, in order to exhibit the bactericidal effect and hydrophilicity, the photocatalyst must be irradiated with light. Therefore, the photocatalyst is unsuitable for the appratuses that are used in various medical environments including a dark place.

The antibacterial action based on the antibacterial processing described in JP1995-313561A (JP-H07-313561A), JP2005-275293A, and JP2003-207864A functions only in the interface between the outer surface having undergone the antibacterial processing and a contaminant. That is, although the propagation of bacteria can be inhibited in the interface, when the thickness of the contaminant is great, it is not easy to inhibit the bacteria from propagating inside the contaminant. In addition, because the action of the antibacterial processing becomes effective only in a state in which the contaminant has been removed, a premise that the contaminant is easily removed is required.

As described above, in the techniques of the related art, a radiation imaging apparatus from which contaminants can be easily removed simply by wiping was not provided, and further improvement was necessary.

Moreover, for radiation imaging apparatuses, it is desired that contaminants can be removed, and the propagation of bacteria resulting from the contaminants can be inhibited.

That is, although there is a demand for a radiation imaging apparatus which enables contaminants having adhered thereto to be easily removed by a simple operation and which can inhibit the propagation of bacteria, a radiation imaging apparatus satisfying such a demand is not known.

The present invention has been made to solve the aforementioned problems, and an object thereof is to provide a radiation imaging apparatus which from which contaminants can be easily removed by only a simple operation and which can inhibit the propagation of bacteria.

The above object is accomplished by the constitution described in the following [1].

[1] A radiation imaging apparatus including a hydrophilized portion provided on at least a portion of the outer surface thereof, in which the hydrophilized portion contains a hydrophilic polymer exhibiting hydrophilicity and an antibacterial agent, and a water contact angle of the surface of the hydrophilized portion is equal to or less than 30°.

The radiation imaging apparatus of the present invention includes a body of the apparatus and peripheral instruments thereof.

That is, in the present invention, the radiation imaging apparatus is provided with the hydrophilized portion which is excellently wetted with water or an aqueous solution even in a dark place which has not been irradiated with light. Accordingly, even when the radiation imaging apparatus, which has been stored in a dark place for a long period time, is wiped by using water or a disinfectant solution such as an aqueous ethanol solution or an aqueous sodium hypochlorite solution immediately after the apparatus is taken out of the dark place, the water or disinfectant solution wets and spreads along the hydrophilized portion and permeates a void between the hydrophilized portion and a contaminant. Therefore, when a contaminant has adhered to the apparatus, the contaminant is easily detached therefrom. As a result, the contaminant can be easily removed within a short period of time.

Furthermore, because the disinfectant solution stays on the outer surface of the radiation imaging apparatus for a long period of time, even when bacteria derived from the contaminant remain, the disinfectant solution comes into contact with the bacteria for a long period of time. Consequentially, a bactericidal ability can be improved further than in the related art.

In addition, when the hydrophilized portion of the radiation imaging apparatus is a portion which is washable with water, for example, the contaminant can also be easily removed with flowing water, in addition to cleaning the apparatus by using water. This is because similarly to the disinfectant solution, flowing water easily permeates a void between the hydrophilized portion and the contaminant.

Needless to say, the contaminant can also be removed from the radiation imaging apparatus just used, and the bactericidal ability can be improved compared to the related art.

Moreover, because the antibacterial agent is contained in the hydrophilized portion, the propagation of bacteria in the hydrophilized portion can be inhibited. Accordingly, even if the bacteria remain, the propagation thereof can be inhibited.

According to the present invention, a hydrophilized portion that is excellently wetted with water or an aqueous solution is provided in a radiation imaging apparatus. Therefore, contaminants that can cause infection can be easily removed by performing a simple operation such as wiping or supplying flowing water thereto.

Furthermore, because an antibacterial agent is contained in the hydrophilized portion, the propagation of bacteria can be inhibited.

BRIEF DESCRIPTION OF THE DRAWINGS

FIG. 5 is a perspective view showing main portions of a radiation imaging apparatus for upright radiography that is a radiation imaging apparatus according to another embodiment of the present invention.

DESCRIPTION OF THE PREFERRED EMBODIMENTS

Hereinafter, the radiation imaging apparatus according to the present invention will be specifically described based on preferable embodiments with reference to the attached drawings.

Figure 1:
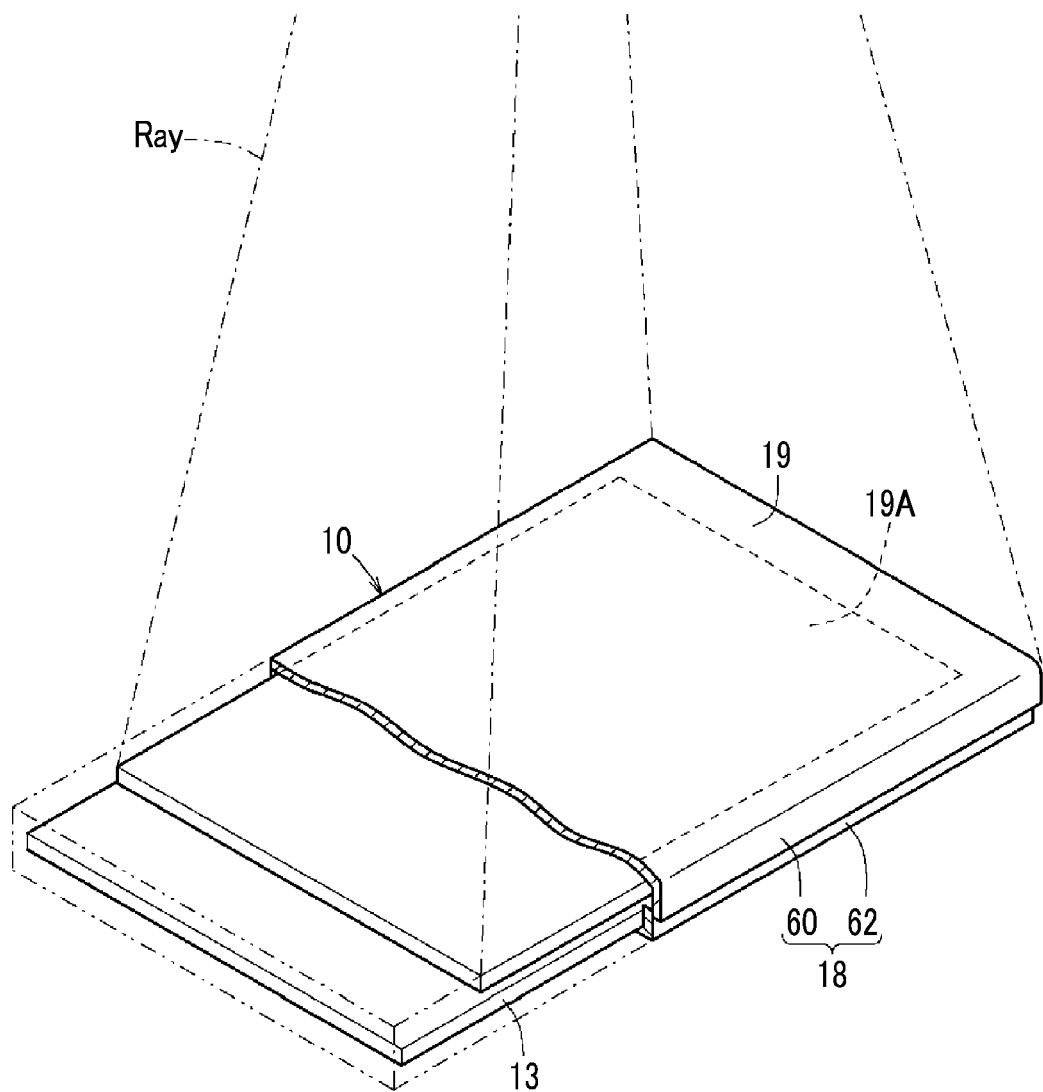
FIG. 1 is a perspective cross-sectional view showing a portion of a portable radiation imaging apparatus as a radiation imaging apparatus according to an embodiment of the present invention.
Figure 2:
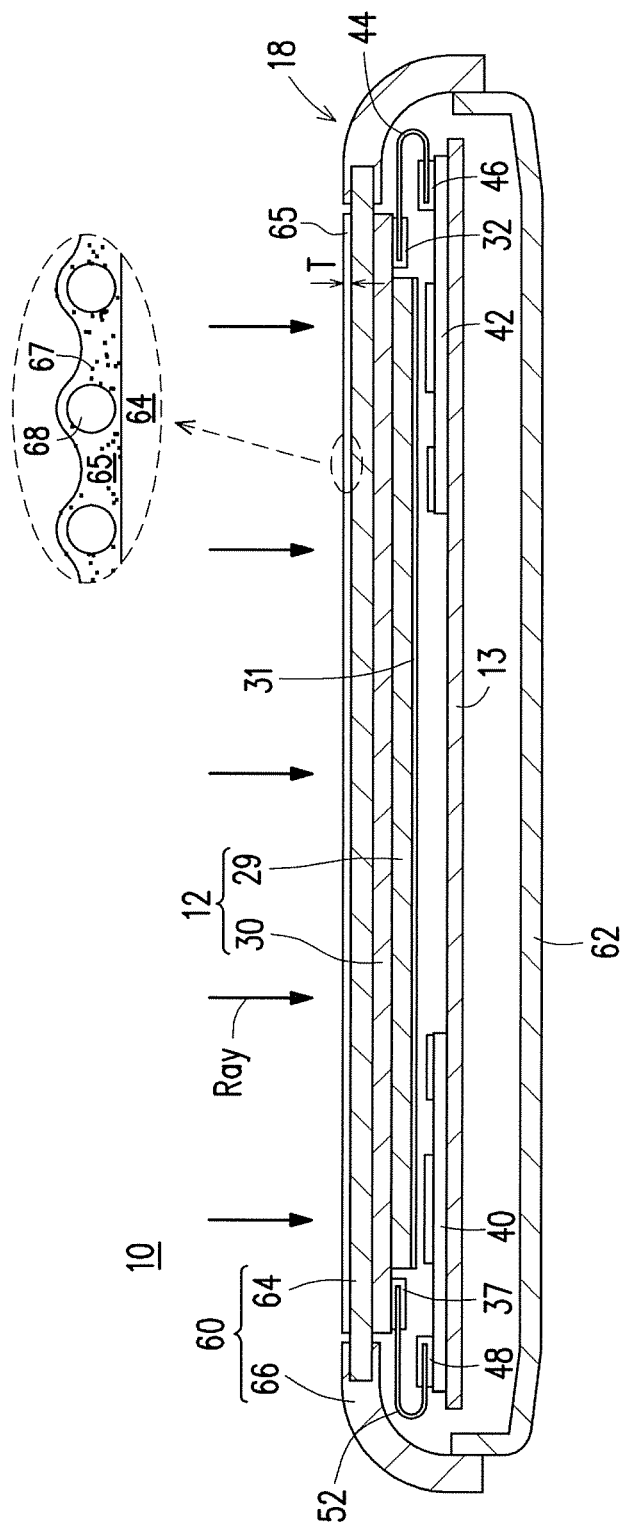
FIG. 2 is a schematic vertical cross-sectional view of the portable radiation imaging apparatus shown in FIG. 1.

FIG. 1 is a perspective cross-sectional view showing a portion of a portable radiation imaging apparatus 10 (so-called electronic cassette) according to a first embodiment. The portable radiation imaging apparatus 10 is a type of radiation imaging apparatus. FIG. 2 is a schematic vertical cross-sectional view of the portable radiation imaging apparatus 10. In the portable radiation imaging apparatus 10, from the side of an irradiation surface 19 irradiated with radiation Ray, a radiation detector 12, which detects the radiation Ray having been transmitted through a patient not shown in the drawing, and a control board 13 which will be described later are provided in this order inside a housing 18. Within the irradiation surface 19, a region in which a radiograph is imaged by the radiation detector 12 is an imaging region 19A.

The radiation detector 12 is constituted with a Thin Film Transistor (TFT) active matrix board (hereinafter, referred to as a TFT board) 30 and a scintillator 29 formed of Gadolinium Oxysulfide (GOS), Cesium Iodide (CsI), or the like that has adhered to the surface of the TFT board 30. In order to prevent the generated light from leaking to the outside, the TFT board 30 may have a light shielding element 31, which shields the generated light, on a surface that is opposite to the surface to which the scintillator 29 has adhered.

In the radiation detector 12, the radiated radiation Ray such as an X-ray is converted into light by the scintillator 29. The generated light enters sensor portions provided in the TFT board 30. The sensor portions receive the generated light from the scintillator 29 and accumulate a charge. Each of the sensor portions is provided with a TFT switch. When the TFT switch is turned ON, according to the amount of charge accumulated in the sensor portion, an electric signal (image signal) showing a radiograph flows in a signal line.

One end of the radiation detector 12 in a signal wiring direction is provided with a plurality of parallel connectors 32 for wire connection, and the other end of the radiation detector 12 in a scanning wiring direction is provided with a plurality of parallel connectors 37. The connectors 32 are connected to signal wirings, and the connectors 37 are connected to scanning wirings.

The control board 13 includes a scan signal control circuit 40 and a signal detection circuit 42. The scan signal control circuit 40 is provided with a connector 48, and the connector 48 is electrically connected to one end of a flexible cable 52. The other end of the flexible cable 52 is electrically connected to the connectors 37. According to this constitution, the scan signal control circuit 40 can output control signals to each of the scanning wirings for turning the TFT switch ON/OFF.

The signal detection circuit 42 is provided with a plurality of connectors 46, and the connectors 46 are electrically connected to one end of a flexible cable 44. The other end of the flexible cable 44 is electrically connected to the connectors 32. The signal detection circuit 42 has a built-in amplification circuit, which is for amplifying the input electric signals, for each of the signal wirings. According to this constitution, the signal detection circuit 42 detects the electric signal input from each of the signal wirings by amplifying the electric signal through the amplification circuit. In this way, the signal detection circuit 42 detects the amount of charge amount in each of the sensor portions as the information on the respective pixels constituting an image.

The housing 18 has the built-in control board 13 which is in the form of a rectangular flat plate and performs various types of control such as the control of the imaging operation of the radiation detector 12 or the control of the communication with external devices. As shown in FIG. 2, the radiation detector 12 is superimposed on the control board 13. In the present embodiment, the radiation detector 12 is disposed such that the TFT board 30 comes into contact with the inner surface of the housing 18 on the side of the irradiation surface 19.

In the housing 18, a front panel 60, which is disposed on the side of the front surface irradiated with the radiation Ray, in other words, a front panel 60 which is disposed on the side coming into contact with an subject is provided to face a back panel 62 (back surface portion) which is disposed on the side opposite to the subject. The front panel 60 is constituted with a top panel 64 and a holding portion 66 that holds the top panel 64. The surface of the top panel 64 on the side of the back panel 62 is provided with the radiation detector 12. At both ends of FIG. 2 in a horizontal direction, the holding portion 66 is curved toward the side of the back panel 62 and forms a portion of a lateral surface portion. Furthermore, at both ends of FIG. 2 in a horizontal direction, the back panel 62 curves toward the side of the front panel 60 and forms a portion of the lateral surface portion. That is, the back surface portion of the housing 18 and a portion of the lateral surface portion of the housing 18 are integrally formed. Herein, it is not necessary to integrally form the back surface portion with only a portion of the lateral surface portion. The back surface portion may be integrally formed with the entirety of the lateral surface portion, and this time, the number of seams of the housing can be reduced, and thus wiping properties are improved.

In the present embodiment, the top panel 64 is formed of carbon, and consequentially, it is possible to secure strength while suppressing the absorption of the radiation Ray. The holding portion 66 and the back panel 62 are formed of an ABS resin.

Within the top panel 64, a region in which a radiograph is imaged by the radiation detector 12 is the imaging region 19A.

In the aforementioned constitution, at least the irradiation surface 19, which comes into contact with a subject (not shown in the drawing) such as a patient at the time of imaging, is provided with the hydrophilized portion 65, as shown in FIG. 2. Herein, not only the irradiation surface 19 but also the back panel 62, the lateral surface portion, and the like may be provided with the hydrophilized portion. Needless to say, a portion that can come into contact with a radiographer, for example, the entirety of the outer surface of the radiation imaging apparatus may be provided with the hydrophilized portion.

In the present invention, when the portable radiation imaging apparatus (electronic cassette) 10 has been inserted under a subject such as a patient, the hydrophilized portion provided on the irradiation surface 19 and the like becomes a surface in contact with the subject. Therefore, in order to make the hydrophilized portion slide easily, a dot shape or a mesh shape may be formed thereon in advance.

Furthermore, for example, it is preferable to perform hydrophilic processing on the surface of the front panel 60 on the side of the irradiation surface 19 such that the hydrophilized portion is provided on the irradiation surface 19. In addition, it is preferable to perform waterproofing processing on the outer surface of the back panel 62 on the side opposite to the irradiation surface 19 (the side opposite to the subject), particularly, on the portion indicated by a reference letter A on both sides of the back panel 62. That is, it is preferable to perform waterproofing processing on a portion A of the outer surface from the seam between the back panel 62 and the holding portion 66 of the front panel 60 constituting a portion of the lateral surface portion of the housing 18 to the region of the edge of the back panel 62 constituting a portion of the back surface portion of the housing 18, such that a waterproofed portion is provided in the portion A.

In this way, by providing the waterproofed portion on the outer surface (the portion A on both sides) of the back panel 62, the portable radiation imaging apparatus (electronic cassette) 10 can be easily inserted under the subject such as a patient.

When a radiation imaging apparatus has a structure in which corners of the electronic cassette incline (curve) as the holding portion 66 of the housing 18 of the portable radiation imaging apparatus (electronic cassette) 10 shown in FIG. 2, a contaminant may drip, and thus the periphery of the electronic cassette may be contaminated. However, in the present invention, a hydrophilized portion is provided on the surface of the front panel 60 on the side of the irradiation surface 19, and a waterproofed portion is provided on the outer surface (the portion A on both sides) of the back panel 62. Therefore, wettability of the surface of the front panel 60 becomes excellent, a contaminant can be prevented from dripping from the holding portion 66 of the front panel 60, and the diffusion of the contaminant can be prevented.

In addition, the embossing processing may be performed on a central portion B of the outer surface of the back panel 62 constituting the back surface portion of the housing 18 such that the central portion B has an embossed structure. Such embossing processing makes it possible to easily insert the electronic cassette 10 under a subject such as a patient.

The hydrophilized portion 65 contains at least a hydrophilic polymer and an antibacterial agent 67, as shown in FIG. 2.

Hereinafter, the materials contained in the hydrophilized portion will be specifically described.

The hydrophilic polymer is a polymer having a hydrophilic group.

The type of the hydrophilic group is not particularly limited, and examples thereof include a polyoxyalkylene group (for example, a polyoxyethylene group, a polyoxypropylene group, or a polyoxyalkylene group formed when an oxyetylene group and an oxypropylene group are bonded to each other in the form of a block copolymer or a random copolymer), an amino group, a carboxyl group, an alkali metal salt of a carboxyl group, a hydroxy group, an alkoxy group, an amide group, a carbamoyl group, a sulfonamide group, a sulfamoyl group, a sulfonic acid group, an alkali metal salt of a sulfonic acid group, and the like.

The structure of a main chain of the hydrophilic polymer is not particularly limited, and examples thereof include polyurethane, a poly(meth)acrylic acid ester, polystyrene, polyester, polyamide, polyimide, polyurea, and the like.

Herein, the poly(meth)acrylic acid ester conceptually includes both a polyacrylic acid ester and a polymethacrylic acid ester.

One of the examples of preferred embodiments of the hydrophilic polymer includes a polymer obtained by polymerizing a monomer having the aforementioned hydrophilic group.

The monomer having a hydrophilic group refers to a compound having the aforementioned hydrophilic group and a polymerizable group. The definition of the hydrophilic group is as described above.

The number of the hydrophilic groups in the monomer having a hydrophilic group is not particularly limited. However, the number of the hydrophilic groups is preferably equal to or greater than 2, more preferably 2 to 6, and even more preferably 2 to 3, because the hydrophilized portion exhibits better hydrophilicity.

The type of the polymerizable group is not particularly limited, and examples thereof include a radically polymerizable group, a cationically polymerizable group, an anionically polymerizable group, and the like. Examples of the radically polymerizable group include a (meth)acryloyl group, an acrylamide group, a vinyl group, a styryl group, an allyl group, and the like. Examples of the cationically polymerizable group include a vinyl ether group, an oxiranyl group, an oxetanyl group, and the like. Among these, a (meth)acryloyl group is preferable.

Herein, the (meth)acryloyl group conceptually includes both an acryloyl group and a methacryloyl group.

The number of the polymerizable groups in the monomer having a hydrophilic group is not particularly limited. However, the number of the polymerizable groups is preferably equal to or greater than 2, more preferably 2 to 6, and even more preferably 2 to 3, because the mechanical strength of the obtained hydrophilized portion becomes better.

One of the examples of preferred embodiments of the monomer having a hydrophilic group includes a compound represented by the following Formula (1).

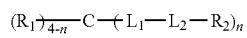

Formula (1)

In Formula (1), $R_1$ represents a substituent. The type of the substituent is not particularly limited. Examples of the substituent include known substituents such as a hydrocarbon group (for example, an alkyl group or an aryl group), which may have a hetero atom, and the aforementioned hydrophilic group.

$R_2$ represents a polymerizable group. The definition of the polymerizable group is as described above.

$L_1$ represents a single bond or a divalent linking group. The type of the divalent linking group is not particularly limited, and examples thereof include —O—, —CO—, —NH—, —CO—NH—, —COO—, —O—COO—, an alkylene group, an arylene group, a heteroaryl group, and a combination of these.

$L_2$ represents a polyoxyalkylene group. The polyoxyalkylene group refers to a group represented by the following Formula (2).

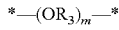

Formula (2)

In Formula (2), $R_3$ represents an alkylene group (for example, an ethylene group or a propylene group). m represents an integer equal to or greater than 2. m is preferably 2 to 10, and more preferably 2 to 6. * represents a binding position.

n represents an integer from 1 to 4.

In order to obtain the hydrophilic polymer, the aforementioned monomer having a hydrophilic group may be concurrently used with other monomers. That is, a hydrophilic polymer, which is obtained by copolymerizing the monomer having a hydrophilic group and other monomers (monomers other than the monomer having a hydrophilic group), may be used.

The other monomers are not particularly limited, and known monomers can be appropriately used as long as they have a polymerizable group. The definition of the polymerizable group is as described above.

Particularly, a polyfunctional monomer having two or more polymerizable groups is preferable, because the mechanical strength of the hydrophilized portion becomes better. The polyfunctional monomer acts as a so-called crosslinking agent.

The number of the polymerizable groups contained in the polyfunctional monomer is not particularly limited. However, the number of the polymerizable group is preferably 2 to 10, and more preferably 2 to 6, because the mechanical strength of the hydrophilized portion becomes better, and the polyfunctional monomer can be handled easily.

Examples of the polyfunctional monomer include trimethylolpropane triacrylate, tetramethylolmethane tetraacrylate, dipentaerythritol hexaacrylate, and pentaerythritol tetraacrylate.

A mixing ratio (the mass of the hydrophilic monomer/the mass of other monomers) of the hydrophilic monomer relative to other monomers (particularly, the polyfunctional monomer) is not particularly limited. However, the mixing ratio is preferably 0.01 to 10, and more preferably 0.1 to 10, because the hydrophilicity of the hydrophilized portion can be easily controlled.

The hydrophilized portion preferably contains the aforementioned hydrophilic polymer as a main component. Herein, the main component refers to a hydrophilic polymer of which the content in the hydrophilized portion is equal to or greater than 50% by mass with respect to the total mass of the hydrophilized portion. The content of the hydrophilic polymer is preferably equal to or greater than 70% by mass, and more preferably equal to or greater than 90% by mass.

The type of the antibacterial agent contained in the hydrophilized portion is not particularly limited, and known antibacterial agents can be used. Examples thereof include an inorganic antibacterial agent and an organic antibacterial agent (preferably a water-soluble organic antibacterial agent). As the antibacterial agent, those exerting a bactericidal effect on pathogenic bacteria represented by *Staphylococcus aureus* and *E. coli* are preferably used.

Examples of the organic antibacterial agent include a phenol ether derivative, an imidazole derivative, a sulfone derivative, a N-haloalkylthio compound, an anilide derivative, a pyrrole derivative, a quaternary ammonium salt, a pyridine-based compound, a triazine-based compound, a benzisothiazoline-based compound, an isothiazoline-based compound, and the like.

More specifically, examples of the organic antibacterial agent include 1,2-benzisothiazolin-3-one, N-fluorodichloromethylthio-phthalimide, 2,3,5,6-tetrachloroisophthalonitrile, N-trichloromethylthio-4-cyclohexene-1,2-dicarboxyimide, copper 8-quinolinolate, bis(tributyl tin)oxide, 2-(4-thiazolyl)benzimidazole <hereinafter, described as TBZ>, methyl 2-benzimidazole carbamate <hereinafter, described as BCM>, 10,10'-oxybisphenoxarsine <hereinafter described as OBPA>, 2,3,5,6-tetrachloro-4-(methylsulfone) pyridine, zinc bis(2-pyridylthio-1-oxide) <hereinafter, described as ZPT>, N,N-dimethyl-N'-(fluorodichloromethylthio)-N'-phenylsulfonamide <dichlofluanid>, poly-(hexamethylenebiguanide)hydrochloride, dithio-2-2'-bis(benzmethylamide), 2-methyl-4,5-trimethylene-4-isothiazolin-3-one, 2-bromo-2-nitro-1,3-propanediol, hexahydro-1,3-tris-(2-hydroxyethyl)-S-triazine, p-chloro-m-xylenol, 1,2-benzisothiazolin-3-one, and the like, but the organic antibacterial agent is not limited to these.

These organic antibacterial agents can be appropriately selected and used in consideration of the hydrophilicity, water resistance, sublimation properties, safety, and the like. Among these organic antibacterial agents, in view of the hydrophilicity, the antibacterial effect, and cost, 2-bromo-2-nitro-1,3-propanediol, TBZ, BCM, OBPA, and ZPT are preferable.

The organic antibacterial agent also includes a natural antibacterial agent. As the natural antibacterial agent, chitosan, which is a basic polysaccharide obtained by hydrolyzing chitin contained in crustaceans such as crabs or shrimps, may be exemplified.

Examples of the inorganic antibacterial agent include mercury, silver, copper, zinc, iron, lead, bismuth, and the like listed in a descending order of the bactericidal effect thereof. Examples of the inorganic antibacterial agent also include those obtained by causing a metal such as silver, copper, zinc, or nickel or a metal ion to be supported on a support. Examples of the support include a silicate-based support, a phosphate-based support, an oxide (for example, glass), potassium titanate, and an amino acid.

More specifically, examples of the inorganic antibacterial agent include a zeolite-based antibacterial agent, a calcium silicate-based antibacterial agent, a zirconium phosphate-based antibacterial agent, a calcium phosphate-based antibacterial agent, a zinc oxide-based antibacterial agent, a soluble glass-based antibacterial agent, a silica gel-based antibacterial agent, an activated carbon-based antibacterial agent, a titanium oxide-based antibacterial agent, a titania-based antibacterial agent, an organic metal-based antibacterial agent, an ion exchanger ceramic-based antibacterial agent, a laminar phosphate-quaternary ammonium salt-based antibacterial agent, antibacterial stainless steel, and the like, however the inorganic antibacterial agent is not limited to these.

Among the above antibacterial agents, metal particles (particularly, copper particles and silver particles are preferable), a silver-based inorganic antibacterial agent, and an organic antibacterial agent are preferable, since the antibacterial effect thereof is strong. As the silver-based inorganic antibacterial agent, ceramic particles supporting silver (silver ceramic particles) are particularly preferable. More specifically, examples of the silver-based inorganic antibacterial agent include silver zeolite in which silver is supported on zeolite as a silicate-based support and an antibacterial agent in which silver is supported on silica gel. Herein, as the organic antibacterial agent, 2-bromo-2-nitro-1,3-propanediol, TPN, TBZ, BCM, OBPA, and ZPT are preferable.

Examples of particularly preferable commercially available silver zeolite-based antibacterial agents include "Zeomic" from Shinagawa Fuel Co., Ltd., "Silwell" from FUJI SILYSIA CHEMICAL LTD., "Bactenon" from JAPAN ELECTRONIC MATERIALS CORPORATION, and the like. In addition, "Novaron" from TOAGOSEI CO., LTD. in which silver is supported on inorganic ion exchanger ceramics, "Atomy Ball" from Shokubai Kasei Kogyo Co., and "San-ai Back P" as a triazine-based antibacterial agent are also preferable. As silver particles, "Nanosilver" from Japan Ion Co. can be selected. Furthermore, it is also possible to select "Bactekiller" or "Bactelite" from Fuji Chemical Co., Ltd. composed of silver ceramic particles obtained by chemically bonding silver to ceramics.

The most preferable embodiments of the antibacterial agent include copper particles, silver particles, copper ceramic particles, and silver ceramic particles that slowly release metal ions. Particularly, silver particles and silver ceramic particles are preferable.

The content of the antibacterial agent in the hydrophilized portion is not particularly limited. However, in view of the balance between the removability of a contaminant and the antibacterial properties, the content of the antibacterial agent is preferably 0.001% by mass to 15% by mass (hereinafter, the unit of the content will be described by using "wt %"), more preferably 0.001 wt % to 10 wt %, and even more preferably 0.001 wt % to 5 wt %, with respect to the total mass of the hydrophilized portion.

When metal particles are used as the antibacterial agent, the content of the antibacterial agent in the hydrophilized portion is preferably 0.001 wt % to 10 wt %, more preferably 0.001 wt % to 5 wt %, even more preferably 0.001 wt % to 1 wt %, and particularly preferably 0.001 wt % to 0.1 wt %, with respect to the total mass of the hydrophilized portion. The content of the antibacterial agent being equal to or greater than 0.001 wt %, the antibacterial effect can be further improved. The content of the antibacterial agent being equal to or less than 10 wt %, the hydrophilicity is not reduced, the temporal properties do not deteriorate, and the antifouling properties are not negatively influenced.

The average particle size of the metal particles (particularly, silver particles) is preferably 1 nm to 100 nm, and more preferably 1 nm to 20 nm. The smaller the particle size of the metal particles is, the greater the ratio of surface area/volume thereof becomes, and accordingly, it is possible to make the hydrophilized portion exhibit antibacterial properties by using an extremely small amount of the antibacterial agent.

When the silver ceramic particles are used, the antibacterial effect can be further improved by making the content of silver ceramic particle to be equal to or greater than 0.1 wt % with respect to the total mass of the hydrophilized portion,. Furthermore, the content thereof being equal to or less than 10 wt %, the hydrophilicity is not reduced, the temporal properties do not deteriorate, and the antifouling properties are not negatively influenced.

An average particle size of the silver ceramic particles is preferably 0.1 μm to 10 μm, and more preferably 0.1 μm to 2 μm.

When the organic antibacterial agent is used as the antibacterial agent, in view of the balance between the removability of a contaminant and the antibacterial properties, the content of the organic antibacterial agent is preferably 1 wt % to 4 wt % with respect to the total mass of the hydrophilized portion.

In the present invention, the antibacterial agent may not be exposed on the surface of the hydrophilized portion.

The hydrophilized portion may contain other components in addition to the aforementioned hydrophilic polymer and antibacterial agent.

For example, the hydrophilized portion 65 may contain a lubricant 68, as shown in FIG. 2. With such hydrophilized portion 65 containing the lubricant 68, concavities and convexities can be formed on the outermost surface thereof, as shown in FIG. 2.

The average particle size of the lubricant 68 is not particularly limited. However, it is preferably 0.5 μm to 30 μm, more preferably 0.5 μm to 20 μm, and even more preferably 6 μm to 10 μm.

The average particle size of the lubricant is obtained by measuring the particle sizes (particle diameters) of 100 random particles by using a microscope (for example, a scanning electron microscope) and calculating the arithmetic mean thereof. When the shape of the lubricant is not a perfect circle, the major axis thereof is measured as the diameter.

The material of the lubricant is not particularly limited. Examples of the material include an inorganic compound (for example, a metal) and a resin, and among these, a resin is preferable. By using a resin, the amount of the radiation Ray absorbed is reduced. Therefore, a problem in that an artifact is superposed on a captured image or a problem in that the radiation reaching the radiation detector 12 in the portable radiation imaging apparatus 10 is attenuated does not easily occur. As a result, it is possible to reduce the exposure dose for the patient as a subject.

A water contact angle of the surface of the hydrophilized portion is equal to or less than 30°. The water contact angle is preferably equal to or less than 21°, and more preferably equal to or less than 15°, because the removability of the contaminant becomes better. The lower limit of the water contact angle is not particularly limited. However, in view of the characteristics of the material used, the lower limit thereof is equal to or greater than 5° in many cases.

If the water contact angle is greater than 30°, the removability of the contaminant becomes poor.

In the present specification, the water contact angle is measured based on a sessile drop method of JIS R 3257: 1999. For measuring the water contact angle, LSE-ME1 (software 2win mini) manufactured by NiCK Corporation is used. More specifically, at room temperature (20° C.), 2 μl as droplets of pure water are dropped onto the surface of the hydrophilized portion which is kept horizontal, and a contact angle at a point in time when 20 seconds has elapsed from the dropping is measured.

The surface of the hydrophilized portion preferably has minute concavities and convexities. With such surface having the minute concavities and convexities, the contact area with a subject can be reduced, and consequentially, the amount of the contaminant, which is derived from sebum and the like, adhering to the hydrophilized portion can be reduced. Furthermore, the contact area with the contaminant can be reduced, and a void can be easily formed between the contaminant and the surface of the hydrophilized portion. Therefore, water or the like easily permeates the void, and consequentially, the removability of the contaminant is improved.

When the hydrophilized portion has the concavities and convexities particularly in a portion which comes into contact with a subject, the contact area with the skin of the subject such as a patient is reduced. Accordingly, the hydrophilized portion feels less sticky, and thus the discomfort the patient experiences at the time of imaging can be reduced.

Surface roughness Ra of the surface of the hydrophilized portion is not particularly limited. However, it is preferably 1 μm to 20 μm, more preferably 2 μm to 15 μm, and even more preferably 3 μm to 6 μm.

The surface roughness Ra is measured based on the method specified in JIS-B0601:2001. Specifically, by using a stylus scanning-type surface roughness tester, the surface roughness of 5 random sites on the surface of the hydrophilized portion is measured, and the average thereof is taken as the surface roughness Ra. It is also possible to measure the surface roughness Ra in the same manner as the stylus scanning-type method by using a laser microscope (for example, VK-X200 manufactured by KEYENCE CORPORATION) equipped with a "roughness meter mode".

The average thickness T of the hydrophilized portion 65 is not particularly limited. However, in view of the removability of the contaminant and the antibacterial properties, the average thickness T of the hydrophilized portion 65 is preferably 0.5 μm to 20 μm, and more preferably 1 μm to 10 μm.

The average thickness of the hydrophilized portion is measured by the following method. A sample piece thereof is embedded in a resin and cut with a microtome so as to obtain a cross section. The cross section obtained by cutting is then observed with a scanning electron microscope so as to measure the average thickness. The thickness in 10 random points in the hydrophilized portion is measured, and the arithmetic mean thereof is calculated.

The method for preparing the hydrophilized portion is not particularly limited, and known methods can be used. For example, it is possible to use a method of forming the hydrophilized portion by coating a predetermined position with a composition containing the aforementioned hydrophilic polymer and antibacterial agent, or a method of sticking a separately prepared polymer film containing the hydrophilic polymer and the antibacterial agent to a predetermined position.

Particularly, the aforementioned method (coating method), in which the hydrophilized portion is formed by forming a coating film by means of coating a predetermined portion with a composition for forming a hydrophilized portion (hereinafter, simply referred to as a "composition" in some cases) containing the monomer having a hydrophilic group and the antibacterial agent and then performing curing processing on the coating film, is preferable, because the thickness of the hydrophilized portion or the concavities and convexities on the surface thereof are more easily adjusted.

The composition contains the aforementioned monomer having a hydrophilic group and the antibacterial agent. However, the composition may contain other components (other monomers described above, a lubricant, and a solvent (water or an organic solvent)).

The composition may also contain a polymerization initiator. With such composition containing the polymerization initiator, polymerization more efficiently proceeds in the coating film, and thus a hydrophilized portion having excellent mechanical strength is formed. The type of the polymerization initiator is not particularly limited, and an optimal type is selected according to the method of curing processing. For example, a thermal polymerization initiator or a photopolymerization initiator is selected. More specifically, examples of the polymerization initiator include aromatic ketones such as benzophenone and phenylphosphine oxide, α-hydroxyalkylphenone-based compounds (IRGACURE 184, 127, 2959, and DAROCUR 1173 manufactured by BASF Corporation, and the like), phenylphosphine oxide-based compounds (MAPO: LUCIRIN TPO manufactured by BASF Corporation, BAPO: IRGACURE 819 manufactured by BASF Corporation), and the like.

The content of the polymerization initiator contained in the composition is not particularly limited. However, it is preferably 0.1 parts by mass to 15 parts by mass, and more preferably 1 part by mass to 6 parts by mass, with respect to a total of 100 parts by mass of the monomer having a hydrophilic group and other monomers.

The coating method of the composition is not particularly limited, and known methods can be used.

Furthermore, the method of the curing processing is not particularly limited, and examples thereof include heating processing or light irradiation processing.

The portable radiation imaging apparatus 10 according to the present embodiment is basically constituted as above. Next, the operation and effects thereof will be described.

In order to obtain a radiograph of a subject, first, at least the irradiation surface 19 of the portable radiation imaging apparatus 10, preferably, the entirety of the outer surface of the housing 18 is cleaned. That is, the housing 18 is wiped with a wiper containing a disinfectant solution. As the disinfectant solution, an aqueous ethanol solution or an aqueous sodium hypochlorite solution is preferably used.

As described above, the outer surface of the housing 18 of the portable radiation imaging apparatus 10 is provided with the hydrophilized portion. Furthermore, in the hydrophilized portion, the water contact angle is equal to or less than 30° even in a dark place not irradiated with light. Consequentially, even when the portable radiation imaging apparatus 10 is stored in a dark place, the outer surface of the housing 18 exhibits sufficient hydrophilicity.

Due to the hydrophilicity, the outer surface of the housing 18 is sufficiently wetted with the disinfectant solution. In other words, the disinfectant solution sufficiently wets and spreads on the outer surface of the housing 18. Accordingly, even if bacteria remain on the outer surface of the housing 18 at this point in time, the disinfectant solution comes into contact with the bacteria for a long period of time. Furthermore, because the hydrophilized portion on the outer surface of the housing 18 contains the antibacterial agent, the antibacterial agent acts on the bacteria. Consequentially, the bactericidal ability can be improved compared to the related art, and the propagation of the bacteria can be inhibited.

That is, even when the portable radiation imaging apparatus 10 is stored in a dark place, the apparatus can be sterilized immediately after being taken out of the dark place.

In a state in which the irradiation surface 19 of the housing 18 of the portable radiation imaging apparatus 10 cleaned as described above is brought into contact with a subject, a physician or a radiological technician (radiographer) irradiates an imaging site of the subject with the radiation Ray from a radiation source. The radiation Ray is transmitted through the imaging site of the subject, passes through the irradiation surface 19 of the portable radiation imaging apparatus 10, and reaches the scintillator 29 of the radiation detector 12.

The scintillator 29 emits fluorescence (visible light) in an amount according to the transmission amount of the radiation Ray. Meanwhile, in the sensor portions provided in the TFT board 30, the charge in an amount according to the amount (emission amount) of the fluorescence is generated and accumulated. The information on the charge is read out by the control portion, and as a result, a radiograph of the imaging site of the subject is obtained.

The portable radiation imaging apparatus 10 is used in an operating room, an emergency room, and the like in some cases. In these cases, the blood or body fluid of a patient (subject) is likely to adhere to the housing 18. In order to remove this type of contaminant, one may consider washing the portable radiation imaging apparatus 10 with flowing water. However, by washing the portable radiation imaging apparatus 10 with flowing water, a battery mounting portion or a connector connecting portion may be wetted with water, and thus the apparatus may be mined.

Therefore, after imaging ends, the housing 18 is wiped with a wiper containing a disinfectant solution such as an aqueous ethanol solution or an aqueous sodium hypochlorite solution. In this case, because the outer surface of the housing 18 is provided with the hydrophilized portion as described above, the disinfectant solution wets and spreads on the outer surface of the housing 18, and the outer surface of the housing 18 is sufficiently wetted with the disinfectant solution.

Therefore, when a contaminant has adhered to the housing 18, water or the disinfectant solution permeates the void between the hydrophilized portion and the contaminant. Consequentially, the contaminant is easily detached from the housing 18. That is, the contaminant can be easily removed.

Furthermore, because the disinfectant solution stays on the outer surface of the housing 18 for a long period of time, even when the bacteria from the contaminant remain on the outer surface, the disinfectant solution comes into contact with the bacteria for a long period of time. In addition, because the hydrophilized portion on the outer surface of the housing 18 contains the antibacterial agent, the antibacterial agent acts on the bacteria. Accordingly, the bactericidal ability can be improved compared to the related art, and the propagation of the bacteria can be inhibited.

As described above, by providing the outer surface of the housing 18 with the hydrophilized portion, it is possible to remove the contaminant from the portable radiation imaging apparatus, which is known to have difficulty in being cleaned with flowing water in the related art, and to easily sterilize the portable radiation imaging apparatus with an improved bactericidal ability when the apparatus is sterilized with a disinfectant solution. In addition, because the hydrophilized portion on the outer surface of the housing 18 contains the antibacterial agent, it is possible to inhibit bacteria from propagating after the portable radiation imaging apparatus is sterilized with the disinfectant solution. Therefore, even if the contaminant remains on the apparatus, due to the action of the antibacterial agent, the propagation of the bacteria can be inhibited.

According to the present embodiment, the housing 18 of the portable radiation imaging apparatus 10 which has been used for imaging can be easily cleaned. Furthermore, because the hydrophilized portion on the outer surface of the housing 18 contains the antibacterial agent, the propagation of bacteria is inhibited, and an advantage that the housing 18 stays clean for a long period of time is obtained.

Figure 3:
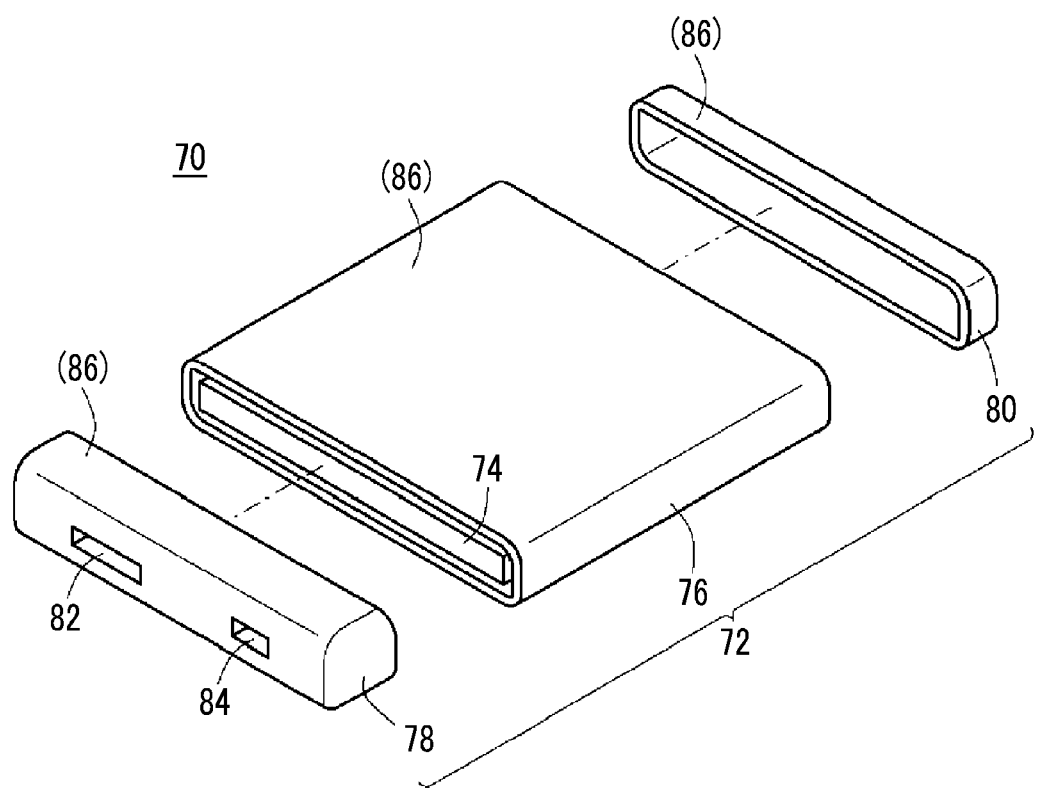
FIG. 3 is a perspective view schematically showing the entirety of another portable radiation imaging apparatus.

FIG. 3 is a perspective view schematically showing the entirety of a portable radiation imaging apparatus 70 according to a second embodiment. The portable radiation imaging apparatus 70 is constituted with a housing 72 and a radiation detector 74 accommodated in the housing.

The radiation detector 74 includes a scintillator, sensor portions, and the like not shown in the drawing. Furthermore, the radiation detector 74 is provided with a charge amplifier IC, a communication portion, and the like (none of these are shown in the drawing).

The housing 72 includes a body member 76 of which both ends in the longitudinal direction are opened and a first cap member 78 and a second cap member 80 that close the opened ends. The body member 76 has a cavity in the inside thereof and is in the form of a so-called cylinder. All of the body member 76, the first cap member 78, and the second cap member 80 may be constituted with a resin material that can transmit radiation.

The first cap member 78 is provided with a battery mounting portion 82 and a connector connecting portion 84. From a battery (not shown in the drawing) mounted on the battery mounting portion 82, a driving current is supplied, and through a connector (not shown in the drawing) mounted on the connector connecting portion 84, wire communication is performed between the portable radiation imaging apparatus 70 and external instruments. Needles to say, wireless communication may be performed instead of the wired communication.

As shown in FIG. 3, the first cap member 78 may be provided with a display portion 88 or the like. The display portion 88 is constituted with an LED lamp or the like, and is used for displaying the driving state and the like of the electronic cassette 10.

The surface on one side of the body member 76, the first cap member 78, and the second cap member 80 constituting the housing 72 form an irradiation surface 86 irradiated with radiation which comes into contact with a subject (not shown in the drawing) such as a patient. At least the portion of the body member 76, the first cap member 78, and the second cap member 80 that comes into contact with the subject (that is, the surface irradiated with radiation) is also provided with a hydrophilized portion composed of a hydrophilic layer similarly to the aforementioned portable radiation imaging apparatus 10. Herein, the hydrophilized portion may be provided not only in the portion of the body member 76, the first cap member 78, and the second cap member 80 that comes into contact with the subject but also in the entirety of the outer surface that can come into contact with a radiographer.

In this case, because the opened ends of the body member 76 accommodating the radiation detector 74 inside thereof are closed by the first cap member 78 and the second cap member 80, the housing 72 in the form of a so-called monocoque is formed and constitutes the portable radiation imaging apparatus 70. Herein, the body member 76 just needs to be able to accommodate the radiation detector 74 inside thereof, and both ends thereof do not have to be opened ends. For example, only one end thereof may be an opened end, and the opened end may be closed by a cap member.

In the portable radiation imaging apparatus 70, the same effect as in the portable radiation imaging apparatus 10 according to the first embodiment is obtained. Herein, in a case in which a portion brought into contact with a subject is very far away from an external instrument-connecting portion such as the connector connecting portion 84, for example, in the case of a radiation imaging apparatus in which the external instrument-connecting portion will not be wetted with water even when the portion brought into contact with a subject is washed with water, the portion brought into contact with a subject may be washed with flowing water. In this case, due to the presence of the hydrophilized portion, water also permeates the void between a contaminant and the outer surface of the apparatus. Accordingly, it is possible to easily remove the contaminant and to inhibit the propagation of bacteria.

In the portable radiation imaging apparatus 70 shown in FIG. 3, the second cap member 80 can be mounted on the body member 76 through fitting, adhesion, or welding. When a structure in which the first cap member 78 is detachably mounted on the body member 76 through adhesion or welding is adopted, the portion other than the first cap member 78 can be dipped into a washing solution. At this time, it is preferable to cap the battery mounting portion 82 and the connector connecting portion 84 with an elastomer so as to prevent these portions from being accidentally wetted with water, although the elastomer is not shown in the drawing. Furthermore, it is preferable to make the first cap member 78 waterproof with an O-ring or the like in advance, although the O-ring is not shown in the drawing.

In this case, because the housing 72 is also provided with the hydrophilized portion, it is possible to easily remove the contaminant and to inhibit the propagation of bacteria.

In the present embodiment, the first cap member 78 may be provided with a detachable handle or a storage handle, although such a handle is not shown in the drawing. Furthermore, a self-adhesive sheet may stick to the housing 72 of a monocoque structure as the portable radiation imaging apparatus 70 shown in FIG. 3, because such a sheet easily sticks to the housing 72.

(Mammography Apparatus)

Figure 4:
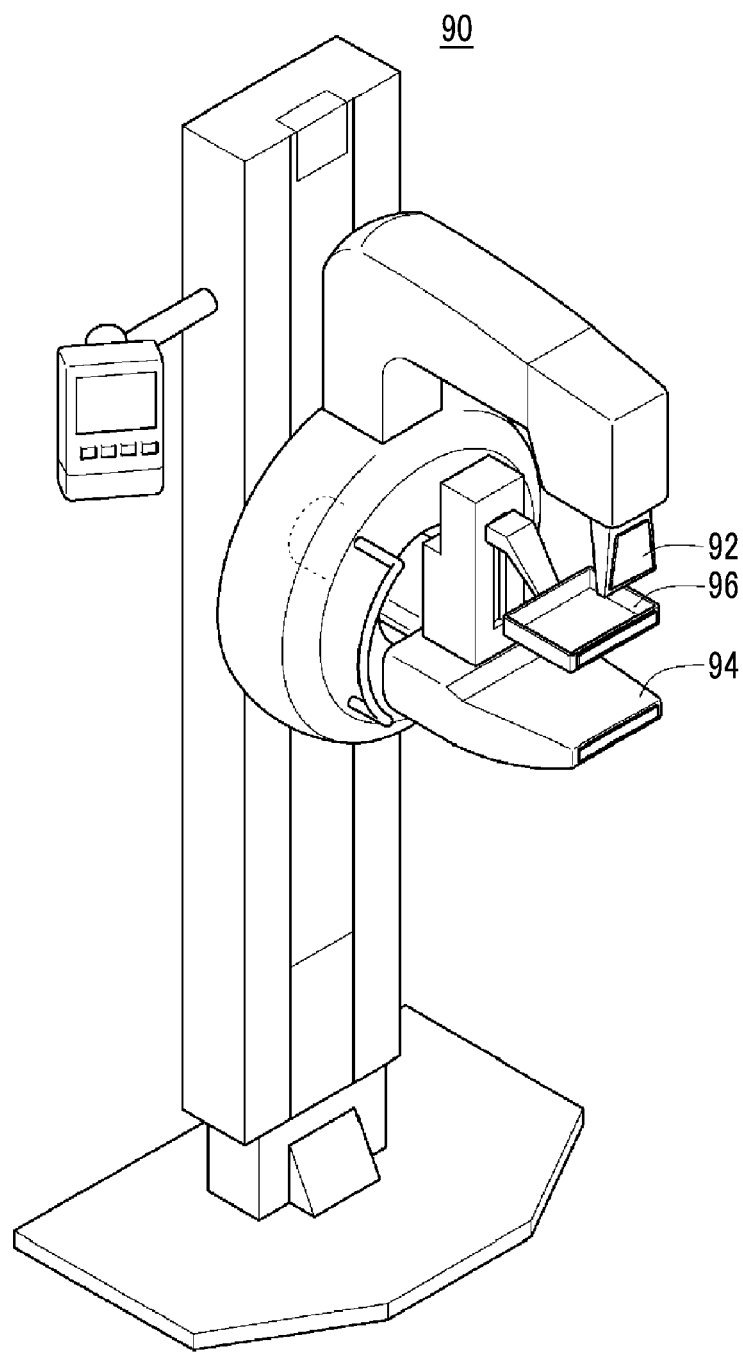
FIG. 4 is a perspective view schematically showing main portions of a mammography apparatus as a radiation imaging apparatus according to another embodiment of the present invention.

The radiation imaging apparatus of the present invention may be a mammography apparatus 90 shown in FIG. 4. In this case, the hydrophilized portion, which contains an antibacterial agent and has undergone antibacterial processing, can be preferably provided in a face guard 92, a breast support 94, or a breast compression plate 96 that is a portion coming into contact with a subject.

The lipstick or sebum of a patient adheres to the face guard 92 in some cases. Moreover, oozing breast milk, blood resulting from a hemorrhage at the time of biopsy (mammotome biopsy), or sebum adheres to the breast support 94 and the breast compression plate 96 in some cases. By providing the hydrophilized portion in the face guard 92, the breast support 94, or the breast compression plate 96, it is possible to remove the lipstick, breast milk, blood, and sebum simply by wiping, and to improve the bactericidal ability compared to the related art because the hydrophilized portion exhibits a high degree of wettability with respect to the disinfectant solution at the time of sterilization.

Furthermore, by providing the mammography apparatus with the hydrophilized portion having undergone antibacterial processing, it is possible to inhibit the propagation of bacteria remaining after wiping or to kill the bacteria. It is also possible to preferably use a method of providing minute concavities and convexities on the surface of the substrate of the hydrophilized portion and a method of adding a lubricant to the hydrophilized portion.

(Radiation Imaging Apparatus for Upright Radiography)

The radiation imaging apparatus of the present invention may be a radiation diagnostic apparatus 100 for upright radiography shown in FIG. 5. In this case, an imaging board 102, which comes into contact with a subject at the time of imaging, or grips 104 and 106 a subject grips at the time of imaging are preferably provided with the hydrophilized portion which contains an antibacterial agent and has undergone antibacterial processing. Furthermore, the hydrophilized portion having undergone antibacterial processing can be preferably provided in other portions including an operation panel portion touched by a radiographer.

(CR Cassette)

Moreover, the outer surface of a CR cassette, which accommodates an imaging plate used for computed radiography (CR) at the time of imaging, can preferably contain the hydrophilized portion which contains an antibacterial agent and has undergone antibacterial processing. In this case, as the portable radiation imaging apparatus, it is preferable that the surface of the imaging surface coming into contact with a subject or the entirety of the outer surface of the CR cassette that can be touched by a radiographer is provided with such a hydrophilized portion.

(Grid)

In addition, the surface of a grid, which is used for removing scattering radiation and improving contrast at the time of imaging performed by using a portable radiation imaging apparatus or a CR cassette, is preferably provided with the hydrophilized portion which contains an antibacterial agent and has undergone antibacterial processing.

The present invention is not limited to the aforementioned examples, and the outer surface of an radiation imaging apparatus which comes into contact with a subject and to which an infectious contaminant can adhere can be provided with the hydrophilized portion which contains an antibacterial agent and has undergone antibacterial processing.

EXAMPLES

Example 1

In the portable radiation imaging apparatus 10, within the housing 18, the surface of the front panel 60, which comes into contact with a patient as a subject, was coated with a composition for forming a hydrophilized portion containing an antibacterial agent that will be described later and then cured (ultraviolet irradiation processing). In this way, a hydrophilized portion which contained an antibacterial agent and had undergone antibacterial processing was provided on the surface of the front panel 60. The average thickness of the hydrophilized portion was about 2 μm. As the top panel 64, a panel in which a polycarbonate sheet (Carboglass CFR110C manufactured by ASAHI GLASS CO., LTD.) had stuck to the surface of a carbon plate was used. The Carboglass CFR110C had a flat and glossy surface.

The surface (the surface coated with the composition for forming a hydrophilized portion) of the front panel 60 was smooth.

(Composition for Forming Hydrophilized Portion)

The composition contained the following components. Herein, a silver ceramic particle dispersion described below was used in such an amount that the content of silver ceramic particles in the hydrophilized portion to be formed (the content (wt % (% by mass)) of the silver ceramic particles with respect to the total mass of the hydrophilized portion) became 0.5 wt %.

| | |
|---|---|
| Monomer having a hydrophilic group: Miramer M4004 (manufactured by Toyo Chemicals Co., Ltd.) | 74 parts by mass |
| Antibacterial agent: a silver ceramic particle dispersion (manufactured by Fuji Chemical Industries, Ltd., an average particle size of 0.8 μm) | |
| Crosslinking agent: A-DPH (manufactured by SHIN-NAKAMURA CHEMICAL CO., LTD.) | 20 parts by mass |
| Polymerization initiator: IRGACURE (manufactured by BASF Corporation) | 3 parts by mass |

Example 2

A hydrophilized portion was provided according to the same procedure as in Example 1, except that as the antibacterial agent in the composition for forming a hydrophilized portion, a fine silver particle dispersion (manufactured by ZEON CORPORATION, an average particle size of 10 nm) was used instead of the silver ceramic particles, in such an amount that the content of the fine silver particles in a hydrophilized portion to be formed (the content (wt %) of the fine silver particles with respect to the total mass of the hydrophilized portion) became 0.002 wt %.

Comparative Example 1

A hydrophilized portion was provided according to the same procedure as in Example 1, except that Miramer M420 was used instead of the monomer having a hydrophilic group. Herein, the monomer did not contain a hydrophilic group.

Comparative Example 2

A hydrophilized portion was provided according to the same procedure as in Example 1, except that an antibacterial agent was not used.

Example 3

A hydrophilized portion was provided according to the same procedure as in Example 1, except that the front panel 60 was prepared by using a mat polycarbonate sheet (Carboglass CFR230C manufactured by ASAHI GLASS CO., LTD.) instead of Carboglass CFR110C manufactured by ASAHI GLASS CO., LTD., 3 parts by mass of a lubricant having an average particle size of 8 μm was additionally added to the composition for forming a hydrophilized portion, and a zinc bis(2-pyridylthio-1-oxide) (ZPT) dispersion (manufactured by DAIWA CHEMICAL INDUSTRIES Co., Ltd.) was used as an antibacterial agent instead of the silver ceramic particles, in such an amount that the content of the antibacterial agent (ZPT) in the hydrophilized portion became 0.5 wt %.

Example 4

A hydrophilized portion was provided according to the same procedure as in Example 3, except that the amount of the zinc bis(2-pyridylthio-1-oxide) (ZPT) dispersion used was changed such that the content of the antibacterial agent was changed to 2.5 wt % from 0.5 wt %.

Example 5

A hydrophilized portion was provided according to the same procedure as in Example 3, except that the amount of the zinc bis(2-pyridylthio-1-oxide) (ZPT) dispersion used was changed such that the content of the antibacterial agent was changed to 5 wt% from 0.5 wt %.

Comparative Example 3

A hydrophilized portion was provided according to the same procedure as in Example 3, except that the amount of the zinc bis(2-pyridylthio-1-oxide) (ZPT) dispersion used was changed such that the content of the antibacterial agent was changed to 9 wt % from 0.5 wt %.

Various evaluations described below were performed on the portable radiation imaging apparatuses obtained in Examples 1 to 5 and Comparative examples 1 to 3 described above.

The water contact angle of the hydrophilized portion in the portable radiation imaging apparatuses obtained in Examples 1 to 5 and Comparative examples 1 to 3 was measured by the aforementioned method. The results are summarized in Table 1.

<Various Evaluations>

(Removability (1))

A substance obtained by staining an unsaturated fatty acid mixture containing oleic acid as a main component of sebum (hereinafter, the substance will be referred to as a stained unsaturated fatty acid mixture) was used as a contaminant. By using the contaminant, evaluation was performed to check how easily the contaminant was removed with flowing water.

On the surface of the front panel (on the hydrophilized portion), the stained unsaturated fatty acid mixture was applied to a region having a diameter of about 2 cm, tap water from shower (a temperature of 25° C.) was brought into direct contact with the region, and the time taken until the contaminant was removed was measured. In Table 1, the time taken until the stained unsaturated fatty acid mixture was removed is described. Herein, when flowing water was used for washing, the evaluation was performed with care such that water did not flow into a connector portion, a screw hole, a battery mounting portion, and the like. The results are summarized in Table 1.

(Removability (2))

Evaluation was performed to check how easily the contaminant was removed by wiping using wet cloth. At this time, the stained unsaturated fatty acid mixture was also used as a contaminant for evaluation.

As described above, on the surface of the front panel (on the hydrophilized portion), a commercially available stained unsaturated fatty acid mixture was applied to a region having a diameter of about 2 cm. Furthermore, BEMCOT manufactured by Asahi Kasei Chemicals Corporation. was dipped into water at room temperature, and the aforementioned region was wiped back and forth with BEMCOT 3 times. Thereafter, whether the stained unsaturated fatty acid mixture remained was visually checked. A case in which the stained unsaturated fatty acid mixture was removed and did not remain was evaluated to be an "A"; a case in which the region needed to be further wiped back and forth not more than 3 times until the contaminant was removed was evaluated to be a "B"; a case in which the region needed to be further wiped back and forth more than 3 times but not more than 10 times until the contaminant was removed was evaluated to be a "C"; and a case in which the contaminant was not removed even after the region was wiped back and forth 10 times was evaluated to be a "D". The results are summarized in Table 1.

(Antibacterial Properties)

The antibacterial properties were evaluated based on the following criteria by measuring the level of antibacterial activity according to the evaluation method described in JIS Z 2801. The higher the level of antibacterial activity, the higher the antibacterial properties. A case in which the level of antibacterial activity was less than 2.0 was evaluated to be a "C (non-antibacterial)"; a case in which the level of antibacterial activity was equal to or greater than 2.0 and less than 5.73 was evaluated to be a "B (antibacterial)"; and a case in which the level of antibacterial activity was equal to or greater than 5.73 was evaluated to be an "A (excellently antibacterial)".

The antibacterial properties 3 hours after the contact with a bacterial solution were also evaluated in the same manner. The results are summarized in Table 1. Herein, "antibacterial properties 3 hours after the contact with a bacterial solution" refer to the antibacterial properties evaluated according to the aforementioned evaluation methods after the hydrophilized portion was brought into contact with a bacterial solution for 3 hours.

Herein, as the bacterial species, $E.\ coli$ as used.

In the following Table 1, "Content of antibacterial agent" represents the content (wt %) of the antibacterial agent with respect to the total mass of the hydrophilized portion.

As is evident from Table 1, the contaminant resulting from the unsaturated fatty acid mixture, which was not removed with flowing water and wiping using wet cloth in Comparative examples 1 and 3, was easily removed in Examples 1 to 5. Generally, a contaminant such as an unsaturated fatty acid is not easily removed simply by being washed with water. However, from Table 1, it was found that by making the water contact angle to be equal to or less than 30° so as to improve the hydrophilicity, the contaminant can be easily removed simply by being washed with water. Furthermore, even when the same test was performed after the radiation imaging apparatus was stored for 1 week in a dark place, the same results were obtained.

The reason is as follows. When water is supplied to the surface of the hydrophilized portion, because the hydrophilized portion has a higher degree of affinity with water than with a contaminant that generally contains a hydrophobic component, water molecules enter a void between the contaminant and the surface of the hydrophilized portion from the edge of the contaminant, and accordingly, the adhesion force between the contaminant and the surface of the hydrophilized portion is reduced. Furthermore, by mechanically wiping the hydrophilized portion by using water pressure resulting from flowing water, wet cloth, or the like, the contaminant is removed. At this time, due to the water permeating the void between the contaminant and the substrate surface, the adhesion force is further reduced compared to the case in which the contaminant having adhered to a less hydrophilic surface is removed in the same manner as described above. Consequentially, the contaminant can be more simply and reliably removed with less effort and by wiping performed a smaller number of times.

It was also confirmed that because the antibacterial agent was contained in the hydrophilized portion, the antibacterial properties were excellent. The hydrophilized portion exhibits excellent antibacterial properties, and accordingly, the antibacterial agent acts on a very small amount of the pathogenic bacteria remaining on the surface. As a result, the propagation of the bacteria can be inhibited, or the bacteria can be killed. Therefore, the likelihood of the infection mediated by the surface of the radiation imaging apparatus can be reduced.

In addition, as shown in Examples 1 to 5, it was confirmed that in a case where the content of the antibacterial agent is

TABLE 1

| | Hydrophilized portion | | | | Evaluation | | | |
|---|---|---|---|---|---|---|---|---|
| | Type of polymer | Type of antibacterial agent | Content of antibacterial agent | Water contact angle | Removability (1) | Removability (2) | Antibacterial properties | Antibacterial properties 3 hours after contact with bacterial solution |
| Example 1 | Hydrophilic polymer | Silver ceramics | 0.5 wt % | 8° | 30 seconds | A | A | A |
| Example 2 | Hydrophilic polymer | Fine silver particles | 0.002 wt % | 8° | 30 seconds | A | A | A |
| Example 3 | Hydrophilic polymer | ZPT | 0.5 wt % | 14° | 18 seconds | A | B | B |
| Example 4 | Hydrophilic polymer | ZPT | 2.5 wt % | 20° | 30 seconds | A | A | B |
| Example 5 | Hydrophobic polymer | ZPT | 5 wt % | 27° | 90 seconds | B | A | B |
| Comparative example 1 | Hydrophilic polymer | Silver ceramics | 0.5 wt % | 80° | Not removed | D | A | C |
| Comparative example 2 | Hydrophilic polymer | — | — | 7° | 30 seconds | A | C | C |
| Comparative example 3 | Hydrophilic polymer | ZPT | 9 wt % | 35° | Remain to some extent | D | A | B | within a predetermined range (0.001 wt % to 5 wt %), the balance between the removability and the antibacterial properties becomes better.

Example 6

A hydrophilized portion was provided according to the same procedure as in Example 1, except that the front panel 60 was prepared by using a mat polycarbonate sheet (Carboglass CFR 230C manufactured by ASAHI GLASS CO., LTD.) instead of Carboglass CFR 110C manufactured by ASAHI GLASS CO., LTD., and a lubricant having an average particle size of 8 μm was additionally added to the composition for forming a hydrophilized portion, in such an amount that the content of the lubricant became 3 wt % with respect to the total mass of the hydrophilized portion.

Example 7

A hydrophilized portion was provided according to the same procedure as in Example 6, except that the amount of the lubricant added was changed such that the content thereof was changed to 5 wt % from 3 wt %.

Example 8

A hydrophilized portion was provided according to the same procedure as in Example 1, except that the front panel 60 was prepared by using a mat polycarbonate sheet (Carboglass CFR 230C manufactured by ASAHI GLASS CO., LTD.) instead of Carboglass CFR 110C manufactured by ASAHI GLASS CO., LTD., and a lubricant having an average particle size of 12 μm was additionally added to the composition for forming a hydrophilized portion, in such an amount that the content of the lubricant became 3 wt % with respect to the total mass of the hydrophilized portion.

Example 9

A hydrophilized portion was provided according to the same procedure as in Example 8, except that the amount of the lubricant added was changed such that the content thereof was changed to 5 wt % from 3 wt %.

Example 10

A hydrophilized portion was provided according to the same procedure as in Example 8, except that the amount of the lubricant added was changed such that the content thereof was changed to 7 wt % from 3 wt %.

Example 11

A hydrophilized portion was provided according to the same procedure as in Example 1, except that the front panel 60 was prepared by using a mat polycarbonate sheet (Carboglass CFR 230C manufactured by ASAHI GLASS CO., LTD.) instead of Carboglass CFR 110C manufactured by ASAHI GLASS CO., LTD., and a lubricant having an average particle size of 16 μm was additionally added to the composition for forming a hydrophilized portion, in such an amount that the content of the lubricant became 5 wt % with respect to the total mass of the hydrophilized portion.

Example 12

A hydrophilized portion was provided according to the same procedure as in Example 11, except that the amount of the lubricant added was changed such that the content thereof was changed to 7 wt % from 5 wt %.

The aforementioned various evaluations were performed on the portable radiation imaging apparatuses obtained in Examples 6 to 12. Furthermore, the following (Evaluation of stickiness) was also performed.

The water contact angle of the hydrophilized portion of the portable radiation imaging apparatuses obtained in Examples 6 to 12 was measured by the aforementioned method.

Moreover, the surface roughness Ra of the surface of the hydrophilized portion in the portable radiation imaging apparatuses obtained in Examples 6 to 12 was measured by the aforementioned method by using VK-X200 manufactured by KEYENCE CORPORATION and a 10× objective lens.

The results are summarized in Table 2.

(Evaluation of Stickiness)

Regarding the stickiness a subject feels when coming into contact with the hydrophilized portion, sensory evaluation was performed. The results were ranked A, B, and C in descending order of perferability. A case in which the hydrophilized portion was markedly sticky or a case in which a subject experienced discomfort when rubbing the hydrophilized portion with the palm was evaluated to be a "C".

In Table 2, "Content of lubricant" represents the content (wt %) of the lubricant with respect to the total mass of the hydrophilized portion.

TABLE 2

| | Hydrophilized portion | | | | | Evaluation | | | | |
|---|---|---|---|---|---|---|---|---|---|---|
| | Substrate of front panel | Average particle size of lubricant | Content of lubricant | Water contact angle | Surface roughness Ra (μm) | Removability (1) | Removability (2) | Antibacterial properties | Antibacterial properties 3 hours after contact with bacterial solution | Evaluation of stickiness |
| Example 1 | C110 | — | — | 8° | 0.5 | 30 seconds | A | A | A | C |
| Example 6 | C230 | 8 μm | 3 wt % | 12° | 2 | 25 seconds | A | A | A | B |
| Example 7 | C230 | 8 μm | 5 wt % | 14° | 4 | 25 seconds | A | A | A | B |
| Example 8 | C230 | 12 μm | 3 wt % | 19° | 6 | 22 seconds | B | A | A | B |
| Example 9 | C230 | 12 μm | 5 wt % | 21° | 10 | 20 seconds | B | A | A | A |
| Example 10 | C230 | 12 μm | 7 wt % | 22° | 12 | 20 seconds | B | A | A | A |

TABLE 2-continued

|  | Hydrophilized portion | | | | | Evaluation | | | | |
| --- | --- | --- | --- | --- | --- | --- | --- | --- | --- | --- |
|  | Substrate of front panel | Average particle size of lubricant | Content of lubricant | Water contact angle | Surface roughness Ra (μm) | Removability (1) | Removability (2) | Antibacterial properties | Antibacterial properties 3 hours after contact with bacterial solution | Evaluation of stickiness |
| Example 11 | C230 | 16 μm | 5 wt % | 26° | 15 | 18 seconds | B | A | A | A |
| Example 12 | C230 | 16 μm | 7 wt % | 30° | 21 | 18 seconds | C | A | A | A |

As shown in Table 2, it was confirmed that when the surface roughness is 2 μm to 15 μm, the balance between the removability of the contaminant, the antibacterial properties, and the stickiness becomes better.

Example 13

A portable radiation imaging apparatus was prepared in the same manner as in Example 1, except that a hydrophilized portion was provided by coating the back panel 62 with the composition for forming a hydrophilized portion instead of the front panel 60.

As a result, it was confirmed that the hydrophilized portion provided on the back panel 62 also exhibits the same removability of the contaminant and the antibacterial properties as in Example 1.

Therefore, when the radiation imaging apparatus is contaminated due to contact with a radiographer or when blood, body fluid, or the like adheres to the apparatus in an operating room or an emergency room, these contaminants can be easily removed in a simple manner.

Examples 14 and 15

(Mammography Apparatus)

In the mammography apparatus 90, the surface of the face guard 92 coming into contact with the face of a patient as a subject was coated with the same composition for forming a hydrophilized portion as used in Example 1 and cured, thereby preparing a mammography apparatus of Example 14. Likewise, the face guard 92 was coated with the same composition for forming a hydrophilized portion as used in Example 2 and cured, thereby preparing a mammography apparatus of Example 15.

At the time of imaging, the sebum or lipstick of a patient or the droplets caused by coughing adhere to the face guard 92 in some cases. However, the face guard 92 of Examples 14 and 15 exhibited excellent removability and antibacterial properties as in Examples 1 and 2.

Example 16

In the mammography apparatus 90, the surface of the breast support 94 and the breast compression plate 96 that comes into contact with the breast of a subject was coated with the same composition for forming a hydrophilized portion as used in Example 1 and cured, thereby providing a hydrophilized portion and preparing a mammography apparatus of Example 16.

At the time of imaging, the skin of the breast of a subject comes into contact with the surface of the breast support 94 and the breast compression plate 96. Furthermore, at the time of imaging, the breast milk oozing due to the compression of the breast or the blood resulting from the hemorrhage that occurs at the time of inserting a needle for biopsy (mammotome biopsy) adheres to the surface of the breast support 94 and the breast compression plate 96 in some cases. The hydrophilized portion of the mammography apparatus prepared as above exhibited excellent removability and antibacterial properties as in Example 1.

Regarding other portions of the mammography apparatus 90, for example, the portions other than the aforementioned portion that can be touched by a patient, a portion such as an operation panel that comes into contact with a radiographer, and other portions to which a contaminant can adhere can also be preferably provided with the hydrophilized portion.

Example 17

(Radiation Imaging Apparatus for Upright Radiography)

In the radiation diagnostic apparatus 100 for upright radiography, the surface of the imaging board 102 was coated with the same composition for forming a hydrophilized portion as used in Example 1 and cured, thereby providing a hydrophilized portion and preparing a radiation diagnostic apparatus of Example 17.

Example 18

In the radiation diagnostic apparatus 100 for upright radiography, the grip 104 and the grip 106 a patient grips were also coated with the same composition for forming a hydrophilized portion as used in Example 1 and cured, thereby providing a hydrophilized portion and preparing a radiation diagnostic apparatus of Example 18.

The hydrophilized portion prepared in Examples 17 and 18 also exhibited excellent removability and antibacterial properties as in Example 1.

The imaging board 102 comes into contact with the skin of a patient. Moreover, when the patient coughs, droplets containing infectious bacteria may adhere to the imaging board 102. Therefore, it is important for the portion to be able to be reliably washed and sterilized in a simple manner.

Furthermore, as shown in Examples 6 to 12, by providing a hydrophilized portion having a predetermined surface roughness Ra on the surface of the imaging board 102, the contaminant can be easily removed, the antibacterial properties can be established, and at the same time, the stickiness can be reduced. Therefore, the patient can feel comfortable when coming into contact with the imaging board.

Meanwhile, regarding the grip 104 and the grip 106, because a patient needs to firmly grip these portions, it is preferable not to provide minute concavities and convexities on the surface of the hydrophilized portion.

Regarding other portions of the radiation diagnostic apparatus 100 for upright radiography, the portion such as an operation panel that comes into contact with a radiographer and portions to which the contaminant adheres can also be preferably provided with the hydrophilized portion.

Example 19

(CR Cassette)

Regarding a cassette case used for computed radiography (CR) using an imaging plate, a cassette case having a hydrophilized portion was prepared according to the same procedure as in Example 1. Because the external appearance of the cassette case is similar to that of the portable radiation imaging apparatus, details thereof will not be described herein. However, the same results were obtained from the cassette case.

What is claimed is:

1. A radiation imaging apparatus comprising a hydrophilized portion provided on at least a portion of an outer surface of the radiation imaging apparatus,
    wherein the hydrophilized portion contains a hydrophilic polymer and an antibacterial agent,
    wherein a water contact angle of a surface of the hydrophilized portion is equal to or less than 30°, and
    wherein the hydrophilized portion contains lubricant particles having an average particle size of 6 µm to 10 µm.
2. The radiation imaging apparatus according to claim 1, wherein a surface roughness Ra of the surface of the hydrophilized portion is 2 µm to 15 µm.
3. The radiation imaging apparatus according claim 1, wherein an average thickness of the hydrophilized portion is 1 µm to 10 µm.
4. The radiation imaging apparatus according claim 2, wherein an average thickness of the hydrophilized portion is 1 µm to 10 µm.
5. The radiation imaging apparatus according to claim 1, wherein a content of the antibacterial agent is 0.001% by mass to 5% by mass with respect to a total mass of the hydrophilized portion.
6. The radiation imaging apparatus according to claim 2, wherein a content of the antibacterial agent is 0.001% by mass to 5% by mass with respect to a total mass of the hydrophilized portion.
7. The radiation imaging apparatus according to claim 1, wherein the antibacterial agent includes at least one selected from the group consisting of ceramic particles carrying silver and silver particles.
8. The radiation imaging apparatus according to claim 1, wherein the hydrophilized portion is provided on a portion which comes into contact with a subject at the time of imaging.
9. The radiation imaging apparatus according to claim 1, wherein the radiation imaging apparatus is a portable radiation imaging apparatus, and
    wherein in a housing of the portable radiation imaging apparatus, the hydrophilized portion is provided on at least a surface which is irradiated with radiation.
10. The radiation imaging apparatus according to claim 9, wherein the hydrophilized portion is provided on either or both of a back surface portion and a lateral surface portion of the housing.
11. The radiation imaging apparatus according to claim 9, wherein the portable radiation imaging apparatus includes a body of the housing of which at least one end is opened, the body having a cylindrical shape, and
    wherein the housing is configured by the body of which the opened end being closed by a cap member.
12. The radiation imaging apparatus according to claim 9, wherein at least the back surface portion of the housing of the portable radiation imaging apparatus and at least a portion of the lateral surface portion of the housing of the portable radiation imaging apparatus are integrally formed.
13. The radiation imaging apparatus according to claim 1, wherein the radiation imaging apparatus is a mammography apparatus, and
    wherein the hydrophilized portion is provided on a portion of a surface of a face guard portion, which portion of the surface comes into contact with a subject.
14. The radiation imaging apparatus according to claim 13, wherein the hydrophilized portion is provided on a portion of a surface of a breast support, which portion of the surface comes into contact with a subject, or on a portion of a surface of a breast compression plate, which portion of the surface comes into contact with a subject.

* * * * *